United States Patent [19]

Brink et al.

[11] Patent Number: 4,978,527
[45] Date of Patent: Dec. 18, 1990

[54] FILM-FORMING EMULSION CONTAINING IODINE AND METHODS OF USE

[75] Inventors: Robert H. Brink, Maplewood; Chi-Ming Tseng, Woodbury, both of Minn.

[73] Assignee: Minnesota Mining and Manufacturing Company, St. Paul, Minn.

[21] Appl. No.: 334,366

[22] Filed: Apr. 10, 1989

[51] Int. Cl.$^5$ .................... A61K 31/74; A61K 31/80; A61K 33/18; A01N 59/10

[52] U.S. Cl. ........................................ 424/78; 424/81; 424/667; 424/668; 424/669; 424/670; 424/671; 424/672; 424/DIG. 13; 424/443; 424/445; 514/937

[58] Field of Search .................. 424/78, 81, 667, 443, 424/445, DIG. 13, 668, 669, 670, 671, 672; 514/937

[56] References Cited

U.S. PATENT DOCUMENTS

| Re. 24,906 | 12/1960 | Ulrich . | |
|---|---|---|---|
| 2,804,073 | 8/1957 | Gallienne et al. | 128/156 |
| 3,216,983 | 11/1965 | Shelanski et al. | 260/88.3 |
| 3,244,658 | 4/1966 | Grosser et al. | 260/29.6 |
| 3,437,647 | 4/1969 | Freifeld | 260/88.3 |
| 3,577,516 | 5/1971 | Gould et al. | 424/46 |
| 3,749,772 | 7/1973 | Cardarelli | 424/81 |
| 4,271,149 | 6/1981 | Winicov et al. | 424/150 |
| 4,310,509 | 1/1982 | Berglund et al. | 424/28 |
| 4,323,557 | 4/1982 | Rosso et al. | 424/28 |
| 4,364,929 | 12/1982 | Sasmor et al. | 424/80 |
| 4,374,126 | 2/1983 | Cardarelli et al. | 424/81 |
| 4,401,795 | 8/1983 | Herman et al. | 526/272 |
| 4,427,631 | 1/1984 | Bunting et al. | 422/22 |
| 4,542,012 | 9/1985 | Dell | 424/28 |
| 4,584,192 | 4/1986 | Dell et al. | 514/635 |
| 4,737,577 | 4/1988 | Brown | 528/501 |

FOREIGN PATENT DOCUMENTS

| 107277 | 5/1984 | European Pat. Off. . |
|---|---|---|
| 130080 | 1/1986 | European Pat. Off. . |
| 2557607 | 7/1976 | Fed. Rep. of Germany . |
| 1465190 | 2/1977 | United Kingdom . |

OTHER PUBLICATIONS

Fredell et al., "Effect of pH and Water Hardness on the Sanitizing Activity of Five Commercial Iodophors", Journal of Food Protection, vol. 48, No. 7 (558–561), Jul. 1985.

Primary Examiner—Merrell C. Cashion, Jr.
Assistant Examiner—Carmen B. Pili-Curtis
Attorney, Agent, or Firm—Donald M. Sell; Walter N. Kirn; Dale A. Bjorkman

[57] ABSTRACT

An emulsion containing a substantially water resistant film-forming copolymer phase and iodine is claimed. The polymer-in-water emulsion forms a film that is a substantially fluid resistant, low tack, flexible film which adheres to skin and releases iodine to skin. The addition of iodate to emulsions having such a film-forming copolymer phase and iodine further enhances stability of the emulsion.

22 Claims, No Drawings

FILM-FORMING EMULSION CONTAINING IODINE AND METHODS OF USE

BACKGROUND OF THE INVENTION

1. Field of the Invention

This invention relates to dermatologically acceptable film-forming emulsions containing iodine. More specifically, it relates to film-forming emulsions useful in promoting asepsis on skin. Methods of using the emulsions are also within the scope of the invention.

2. Description of the Background Art

In order to reduce the risk of infection in patients, it has become standard practice to topically apply an antimicrobial agent to compromised areas such as surgical incision sites, wounds, burned areas, catheterization sites and injection sites. Topical application of antimicrobials has been utilized to reduce the bacteria count on skin in the area of application.

Topical application of antimicrobial agents has been accomplished using, for example, solutions, tissues, lotions, and ointments. Because microorganisms may survive the initial application of the antimicrobial agent, it is often necessary to reapply the agent in order to provide continued asepsis. Also, because antimicrobial agents are often water soluble, and therefore, subject to removal from the application site by water or bodily fluids, reapplication of the antimicrobial agent may be necessary to assure continued bactericidal activity. In particular, polyvinylpyrrolidone, which is widely utilized as a carrier for the broad spectrum antimicrobial iodine, is water soluble and is rapidly washed away from skin by irrigation or bodily fluids.

Increasing the water and bodily fluid resistance of topically applied antimicrobial agents and thereby increasing the substantivity and length of bactericidal activity has been a long standing goal in the art. In particular, there are several examples of inventions with the aim of improving the substantivity of the N-vinyl-pyrrolidone/iodine complex. Compositions that are able to form a water insoluble film can, in addition to providing long lasting antimicrobial activity, also provide a protective layer for sensitive tissue such as is present in burn wounds.

Organic solvents such as ethyl alcohol or isopropyl alcohol are often used as the antimicrobial agent and/or as the solvent carrier for other antimicrobial agents. Alcohols and other organic solvents can be irritating to skin tissue and are not suitable for use on sensitive tissues such as burn wound sites and mucosal tissue. Often the vapors of the organic solvents are toxic and/or flammable.

The addition of iodine to colloids or emulsions has in the past been found to be destabilizing to the system. For example, U.S. Pat. No. 4,364,929 to Sasmor et al. discloses an aqueous germicidal colloidal lubricating gel comprising iodine and a gel forming colloid. In the background discussion at column 2, lines 37-42, the corrosive and oxidizing nature of iodine is discussed, noting that it destroys the stability of most pharmaceutical compositions and, in particular, colloidal lubricating gels. The patentees disclose that when iodine is added to a carbohydrate polymer in the presence of a substrate capable of forming an iodophor, such as povidone, a stabilizing effect is observed which prevents the destruction of the colloidal properties of the carbohydrate polymer by iodine.

Polyvinylpyrrolidone containing polymers complexed with iodine have been utilized as film-forming compositions. These compositions require high amounts of vinylpyrrolidone with correspondingly high amounts of iodine to render the polymer insoluble in water. These films would be extremely dark, so that viewing through the film would be virtually impossible. Due to the relatively high iodine content of the prior art systems, applicants expect that these emulsions would have a relatively short shelf life.

European Patent No. 107,277 discloses an antimicrobial film consisting of 30 to 80 wt. % vinyl acetate and 20 to 70 wt. % vinylpyrrolidone copolymer combined with iodine and/or bromine to provide 2 to 25% available halide in the final product. The copolymer may be prepared by solution, suspension, precipitation or emulsion polymerization and is complexed by contacting with a 10 to 50% solution of halogen in an alcohol solution. The complex product is diluted with water and azeotropically distilled to form a viscous liquid product. The product may be used in its viscous state as a coating or can be diluted with an inert solvent such as water or alcohol for use as a liquid or aerosol spray.

German Patent No. 2,557,607 discloses the preparation of a water insoluble copolymer having vinylpyrrolidone as one of the constituent monomers. The copolymer is converted into an insoluble addition compound by using a sufficient amount of iodine regardless of the initial solubility of the starting polymer. The amount of iodine required for this purpose is usually above 60% by weight based on the weight of the polymer. If the starting polymer is water insoluble, the iodine content of the adduct is generally in the range of from 0.1 to 50% by weight, based on the weight of the polymer. The formation of a film from an emulsion of the iodophor polymer is disclosed at the paragraph bridging pages 13 and 14.

A disadvantage of emulsion system film-forming compositions long recognized in the art is that such systems are expected to require comparatively long dry times. British Patent No. 1,465,190 describes polymer in water emulsions which "... dry, i.e., form films, rapidly when placed on the skin, normally within about 4 to 6 minutes." The dry time recited above that the British patentees considered to be rapid is now considered to be too long for practical application. Surgeons and nurses prefer that any film-forming presurgical prep be dry to the touch in 2.5 minutes or less, and preferably less than 2 minutes.

U.S. Pat. No. 2,804,073 to Gallienne et al. discloses a film-forming composition. This composition can be either a polymer in organic solvent solution or a polymer-in-water emulsion. Organic solvents are used when dry times on the order of 5 minutes are desired, while a water emulsion is used when it is desired to increase the dry time to about 15 minutes or more. The cohesive strength of these films is greater than their adhesive strength, thus enabling them to be peeled intact from the skin to which they are applied.

U.S. Pat. No. 3,244,658 to Grosser et al. discloses the preparation of a stable aqueous emulsion containing a polymeric N-vinyl lactam. This emulsion provided a film which apparently was a mixture of a water soluble N-vinyl lactam homopolymer and a benzene soluble acrylic ester homopolymer. The patentees found that copolymerization of a N-vinyl lactam monomer and acrylic ester monomer in about equal amounts yielded an unstable emulsion, even without addition of $I_2$. As disclosed in column 3, lines 52-62, the polymer formed by the process of the patent is a graft copolymer of an acrylic ester on a polymeric N-vinyl lactam substrate. No disclosure additionally complexing iodine with this polymer is provided.

U.S. Pat. No. 4,271,149 to Winicov et al. discloses germicidal iodine compositions comprising an aqueous solution of elemental iodine and at least one organic substance which slowly reacts with iodine. Iodine loss during the extended storage of the composition is controlled by providing iodide ion and iodate ion in a controlled pH range so that lost elemental iodine is restored by the reaction of iodate and iodide in the presence of hydrogen ions.

U.S. Pat. No. 4,374,126 to Cardarelli et al. discloses a film-forming antimicrobial material which comprises an alcohol soluble carboxylated polyacrylate, an antimicrobial agent such as bacitracine or iodine, a difunctional amide as a crosslinking agent and an adhesion promoting material. As disclosed at column 4, lines 53-61, the film-forming material is prepared in an ethyl alcohol and water solution.

U.S. Pat. No. 4,542,012 to Dell discloses a film-forming polymer which is the reaction product of (1) a prepolymer having a plurality of isocyanate functionalities, (2) a polyvinylpyrrolidone polymer and (3) a chain extender for the prepolymer and the polyvinylpyrrolidone polymer. This film-forming polymer is complexed with an antimicrobial agent, specifically iodine. The film-forming composition is applied to the skin as a solution in a volatile solvent such as ethanol or isopropanol.

U.S. Pat. No. 4,584,192 to Dell et al. discloses a film-forming copolymer consisting of copolymerized A, B and C monomers wherein A is an acrylic acid ester having 2 to 14 carbon atoms or is a methacrylic acid ester of 7 to 18 carbon atoms, B is a methacrylic acid ester of 1 to 6 carbon atoms, and C is an N-vinyl lactam which is from 1 to 15% of the total weight of all monomers in the copolymer. This film-forming copolymer composition is complexed with iodine. The composition is applied to the skin from a fugitive solvent, such as ethanol, isopropanol and acetone. Application of these solutions of water immiscible polymers in solvent to wet surfaces can result in precipitation of the copolymer and poor film formation. Organic solvents are utilized due to the need to have a carrier for the water insoluble copolymer and in order to provide a quick formation of dry films through the use of rapidly drying, volatile solvents.

The prior art has not provided a film-forming composition which is totally acceptable from the standpoint of convenience, nonirritation, nonflammability even before drying and safety and efficacy in promoting asepsis on skin. A good film-forming composition should be dermatologically acceptable and capable of application conveniently in a water based mixture which dries quickly on skin. The film resulting from application of such an emulsion should be water and body fluid resistant and substantially tack free, and should permit facile transmission of water vapor therethrough. The film should be clear to permit, for example, viewing of the site where an incision will be made during a surgical procedure. It should further adhere suitably to skin and be capable of releasing an antimicrobial agent onto the skin over a period of time. The film should be soluble in a dermatologically acceptable solvent such as a lower alkyl alcohol which may be used as or in a remover solution which is employed to remove the film when desired.

The film-forming emulsion of the present invention successfully meets the aforementioned criteria.

SUMMARY OF THE INVENTION

The present invention provides a film-forming emulsion comprising:

(a) a substantially water resistant film-forming copolymer phase comprising A, B and C monomers wherein A is a "soft" monomer wherein the corresponding homopolymer has a glass transition temperature ($T_g$) of less than about $-15°$ C., and is present as about 15 to 80% of the total weight of all monomers in the copolymer, B is a "hard" monomer wherein the corresponding homopolymer has a $T_g$ of more than about $-5°$ C., and is present as about 20 to 70% of the total weight of all monomers in the copolymer, and C is a monomer capable of complexing iodine and delivering it to the skin and is present as about 1 to 15% of the total weight of all monomers in the copolymer;

(b) about 0.05 to 15% of iodine based on total emulsion weight;

(c) an effective amount of an emulsifying agent; and (d) about 30 to 95% by weight of water. The monomers in the copolymer phase are selected such that the emulsion, when applied to human skin in an amount sufficient to form a film having a thickness of about 0.01 mm., dries in less than five minutes to form a film having the properties of (i) being hydrophobic, as determined by scrubbing the film using light finger pressure with a saline-soaked gauze for at least 40 scrubs with no observable removal of film or loss of iodine color, and (ii) being capable of elongating at least about 5% before breaking.

This composition is dermatologically acceptable, and, when applied to skin, is capable of forming a clear, substantially fluid resistant, substantially tack free flexible film which adheres to skin and releases iodine to the skin.

A preferred copolymer composition additionally comprises 0.1-100% iodate based on added iodine. The addition of iodate provides a surprisingly stable emulsion.

The method of using the emulsion of the present invention to cover skin with a film exhibiting microbicidal activity and to thereby promote asepsis comprises the steps of:

(a) applying the emulsion to the skin;

(b) allowing the emulsion to dry to form a film; and (c) allowing the film to remain on the skin to promote asepsis.

The present invention solves the problems associated with prior art compositions by providing a film-forming emulsion which exhibits the following characteristics. The film-forming emulsion is dermatologically acceptable and may be applied to skin conveniently as a water based emulsion. Because the emulsions of the present invention are water based mixtures, they are nonflammable, nonirritating and may be applied to wet tissue. Even though water is a slow drying substance, the emulsions of the present invention dry to form low tack or tack free films in a surprisingly short time (less than about 5 minutes).

The emulsions of the present invention also provide iodine containing emulsions of surprising stability at room temperature and elevated temperature (49° C). This surprising stability is particularly enhanced by incorporating iodate anion in the emulsions.

The film resulting from the application of the emulsion is substantially fluid resistant, tack free or low tack, and permits facile transmission of moisture vapor therethrough. Further, the film is clear and therefore allows viewing of the underlying skin. Iodine is released to the skin upon contact of the emulsion with the skin, and continues after the film is formed. The adhesion of the film to skin is preferably significantly higher than the cohesive strength, particularly at the thin coatings which are particularly suited for the present invention. This results in films that cannot be peeled intact from the skin, thus reducing the possibility of film lift at the incision site during surgical incision and retraction. The film is soluble in dermatologically acceptable lower alkyl alcohols such that it may be removed conveniently using a remover solution comprising such an alcohol. The composition of the invention is particularly suitable for use as a presurgical skin preparation. The composition is also particularly suitable for promoting asepsis in and around puncture wounds such as sites of injection or catheterization. The compositions of the invention may also be used in liquid bandages, coating for percutaneous access device sites, stoma seals, various general hospital uses, teat dips, and liquid gloves for medical use or food handling, and the like. Because the emulsions of the present invention are water based, some embodiments may be used on mucosal or burned tissue.

DETAILED DESCRIPTION

The emulsion of the present invention is dermatologically acceptable and provides a film which is clear and substantially fluid resistant. As used herein, the term "dermatologically acceptable" means that the emulsion does not cause either substantial irritation to skin or patient sensitization as the result of contact therewith. The term "clear" means that a film provided by the emulsion of the invention is transparent and free of turbidity. The phrase "substantially fluid resistant" means that a film retains its integrity when contacted with body fluids (e.g. blood and perspiration), irrigation fluids and the like even when the film is rubbed lightly. The word "emulsion" is intended to include those emulsions prepared by emulsion and suspension polymerization, emulsions prepared by post emulsification of polymers prepared in solution or bulk, natural lattices and emulsions prepared by dispersion.

An appropriate copolymer system for use as a film-forming polymer in the present invention is a copolymer comprising copolymerized A, B and C monomers as follows:

A is a "soft" monomer wherein the corresponding homopolymer has a $T_g$ of less than about $-15°$ C. and A is present as about 15 to 80% of the total weight of all monomers in the copolymer. Typically, A is a monomer that provides flexibility, elongation and adhesiveness to skin in the copolymer. The A monomer usually provides the degree of hydrophobicity which results in the desired resistance to body fluids.

B is a "hard" monomer wherein the corresponding homopolymer has a $T_g$ of more than about $-5°$ C., and preferably more than about 20° C., and B is present as about 20 to 70% of the total weight of all monomers in the copolymer. Typically, the B monomer is a monomer that provides tensile strength and also reduces tack in the copolymer.

The C monomer is a monomer capable of complexing iodine and delivering it to the skin. For example, C is an N-vinyl lactam or monomers containing polyether functionalities. The C monomer is present in an amount by weight of about 1 to 15% of the total weight of all comonomers in the copolymer.

The A monomer is typically a monomeric acrylic or methacrylic acid ester of an alkyl alcohol containing a single hydroxyl, the alcohol being further described as having from 2 to about 14 carbon atoms when the A monomer is an acrylic acid ester, and about 7 to 18 carbon atoms when the A monomer is a methacrylic acid ester.

Examples of suitable acrylic acid esters for use as the A monomer include the esters of acrylic acid with non-tertiary alcohols such as ethanol, 1-butanol, 2-butanol, 1-pentanol, 2-pentanol, 3-pentanol, 2-methyl-1-butanol, 1-hexanol, 2-hexanol, 2-methyl-1-pentanol, 3-methyl-1-pentanol, 2-ethyl-1-butanol, 3,5,5-trimethyl-1-hexanol, 3-heptanol, 1-octanol, 2-octanol, iso-octyl alcohol, 2-ethyl-1-hexanol, 1-decanol, 1-dodecanol, 1-tridecanol, 1-tetradecanol and the like.

Examples of suitable methacrylic acid esters for use as the A monomer include the esters of methacrylic acid with non-tertiary alcohol such as 3-heptanol, 1-octanol, 2-octanol, iso-octyl alcohol, 2-ethyl-1-hexanol, 1-decanol, 1-dodecanol, 1-tridecanol, 1-tetradecanol, 1-octadecanol and the like.

Other examples of soft monomers that can be used for the A monomer component are monomers having the requisite $T_g$ values including dienes, such as butadiene and isoprene; acrylamides, such as N-octylacrylamide; vinyl ethers, such as butoxyethylene, propoxyethylene and octyloxyethylene; vinyl halides, such as 1,1-dichloroethylene; and vinyl esters such as vinyl versatate, vinyl caprate and vinyl laurate.

The preferred A monomer is selected from the group consisting of n-butyl acrylate, iso-octyl acrylate and lauryl methylacrylate (the methacrylic acid ester of 1-dodecanol).

It is to be understood that the film-forming copolymer may comprise a single type of A monomer or may comprise two or more different A monomers.

Monomer B of the film-forming copolymer is typically a monomeric methacrylic acid ester of an alkyl alcohol containing a single hydroxyl. The alcohol contains from 1 to about 6 carbon atoms, and preferably 1 to about 4 carbon atoms.

Examples of suitable monomers for use as the B monomer include the esters of methacrylic acid with non-tertiary alcohols such as methanol, ethanol, 1-propanol, 2-propanol, 1-butanol, 2-butanol, 1-pentanol, 2-pentanol and 3-pentanol.

Other examples of hard monomers that can be used for the B monomer component are monomers having the requisite $T_g$ values include methacrylates having a structure other than delineated above, such as benzyl methacrylate, cyclohexyl methacrylate and isobornyl methacrylate; methacrylamides, such as N-t-butylmethacrylamide; acrylates, such as isobornyl acrylate; acrylamides, such as N-butylacrylamide and N-t-butylacrylamide; diesters of unsaturated dicarboxylic acids, such as diethyl itaconate and diethyl fumarate; vinyl nitriles, such as acrylonitrile, and methacrylonitrile; vinyl esters, such as vinyl acetate and vinyl propionate;

and monomers containing an aromatic ring such as styrene; α-methyl styrene and vinyl toluene.

The preferred B monomer is selected from the group consisting of methyl methacrylate and ethyl methacrylate.

It is to be understood that the film-forming copolymer may comprise a single type of B monomer or may comprise two or more different B monomers.

The C monomer is a monomer capable of complexing iodine and delivering it to the skin. Examples of C monomers include N-vinylpyrrolidone or monomers containing polyether functionalities such as polypropylene oxide and polyethylene oxide.

The preferred class of C monomers is N-vinyl lactams which are capable of complexing iodine. Examples of suitable N-vinyl lactams which may be employed include those disclosed in U.S Pat. No. 3,907,720 (Field et al.) incorporated herein by reference. That patent discloses, for example, N-vinyl-substituted derivatives of the following lactams 3,3-dimethyl-1-pyrrolidone, 4,4-dimethyl-2-pyrrolidone, 3,4-dimethyl-2-pyrrolidone, 3-ethyl-2-pyrrolidone, and 3,5-dimethyl-2-pyrrolidone. The preferred N-vinyl lactam is N-vinylpyrrolidone.

It is to be understood that the film-forming copolymer may comprise a single type of C monomer or may comprise two or more different C monomers.

The relative water resistance of the ultimate film may be determined by the selection of comonomers to be used with the iodine complexing comonomer and by adjusting the ratio of water insoluble comonomers to water soluble comonomers that form the film. The resulting copolymers give films which have high moisture vapor transmission rates and which are water insoluble.

Iodine is incorporated as an antimicrobial agent, and is present in these emulsions in a effective amount (i.e. an amount which exhibits bactericidal activity when applied to skin). As a general statement, film-forming emulsions comprising about 0.05 to 15% by weight of iodine based on the total weight of the emulsion provide films exhibiting suitable antimicrobial activity. Preferred film-forming emulsions for use as pre-surgical patient skin preparations are those containing iodine in an amount by weight of about 0.10 to 5% by weight based on the total emulsion weight, and particularly preferred emulsions contain iodine in an amount by weight of about 0.25 to 2% by weight based on the total solids weight. When the emulsion is used on extremely sensitive tissue such as eyes or burn wounds, iodine may be used at a lower level. Preferred film-forming emulsions for use on sensitive tissue are those containing iodine in an amount of about 0.05 to 0.25% by weight based on the total solids weight.

It is preferred that emulsions that contain iodine also contain iodide ion. While not wishing to be bound to any particular theory, it is believed that iodide ion increases the stability of the complex involving iodine and an N-vinyl lactam residue, thereby reducing the loss of iodine over time. The iodide ion is preferably added as an inorganic salt, such as sodium or potassium iodide, in about 5% to 300% by weight based on added iodine.

It has surprisingly been learned that the use of iodate in the emulsions containing a substantially water resistant film-forming copolymer phase that is capable of forming complexes with iodine significantly increases the resistance of said emulsions to phase separation, coagulation, gelation, precipitation and other forms of physical and chemical destabilization at room temperature and at 49° C. It was not anticipated by the prior art that iodate ions would significantly increase the stability of polymer-in-water emulsions containing iodine. The iodate ion is preferably added as an inorganic salt, such as sodium or potassium iodate in about 0.1% to 100% by weight based on added iodine, and more preferably in an amount by weight of about 1 to 30% based on added iodine.

Thus, a particularly preferred composition of the present invention comprises (a) a substantially water resistant film-forming copolymer phase comprising about 50 to 60% by weight based on the total copolymer weight of iso-octyl acrylate, about 35 to 45% by weight based on the total copolymer weight of methyl methacrylate, and about 5 to 10% by weight based on the total copolymer weight of N-vinylpyrrolidone;

(b) about 1-2% of iodine based on total emulsion weight;

(c) an effective amount of an emulsifying agent;

(d) about 55 to 85% by weight of water based on total emulsion weight;

(e) about 5 to 100% by weight of iodide based on added iodine; and (f) about 2.5 to 20% by weight of iodate based on added iodine.

Emulsifiers commonly used in emulsion polymerization, including anionic, nonionic, nonionic-anionic, amphoteric types and combinations of the above types, may be used as the emulsifying agent. An appropriate emulsifier for use in the present system will make a stable latex; will be compatible with iodine, iodide and iodate; will be physiologically acceptable and will allow appropriate control of viscosity and pH of both the latex and the final product. Because negatively charged latex particles are to be used in this system, anionic and nonionic plus anionic emulsifiers are expected to have the highest probability of success, with the nonionic emulsifier used in combination with an anionic emulsifier to give better tolerance to the electrolyte. Particularly useful emulsifiers include anionic species such as alkyl sulfates, sarcosinates, alkyl sulfosuccinates, and fatty acid soaps. Nonionic emulsifiers include polyoxyethylene sorbitan fatty esters, ethoxylated glycerides, and polyglycerol esters of fatty acids. Emulsifier content should be chosen to stabilize the emulsion without inhibiting film-forming. Typically, emulsifier content of about 0.5 to 5.0% by weight based on added monomer mixture is suitable, with emulsifier content of about 1.0% to 2.0% preferred.

The emulsions may consist of any ratio of solids that provides sufficient material to form a film and allows the emulsion to be applied. Preferably, solids are present in an amount of between about 15 to 30% by weight total emulsion. High solids ratios may tend to decrease stability of the emulsions.

The pH of the emulsions is preferably between about 3 and 8, more preferably between about 5 and 7. The pH of the emulsions may be adjusted by the addition of appropriate acidic or basic species and/or optionally by the use of a buffer system.

The emulsion of the present invention may further include conventional additives such as plasticizers, colorants, tackifiers and/or stabilizers to achieve desired properties.

While the emulsion of the present invention is applied to the skin as a polymer-in-water emulsion, small amounts of organic solvent may be present if the resulting emulsion is nonflammable and nonirritating.

For the present invention, it is necessary that the copolymers be available as polymer-in-water emulsions. This may be accomplished by preparing the copolymers from the appropriate monomers via emulsion polymerization or by post-emulsification of solution or bulk prepared polymers.

The film-forming copolymer emulsions may be prepared using conventional emulsion polymerization methods. For laboratory tests, samples can be prepared from batch process polymerization or semi-continuous process polymerization, two commonly used modes of emulsion polymerization. In the former, all the ingredients including monomers, emulsifiers, initiator and water are added to the reactor before the reaction starts. In the latter, only part of monomers are used to start the polymerization and the rest of the monomers are added to the reactor over a period of time to achieve more homogeneous incorporation of the comonomers. The semi-continuous process has been found to render a more stable emulsion product.

Potassium persulfate and ammonium persulfate are commonly used initiators. Other peroxy compounds may also be used. Suitable polymerization temperatures are in the range of 50° to 80° C. Near the end of polymerization, a monomer scavenger such as vinyl acetate may be used to reduce residual monomer content as taught by U.S. Pat. No. 4,737,577 (Brown, et. al.). Vacuum can also be applied to the reactor to reduce residual monomer content.

The emulsion of the invention desirably can be sterilized by exposure to a dose of about 2.5 megarads of gamma irradiation without substantial alteration of the physical appearance or physical properties such as low tackiness and fluid resistance. Such irradiated emulsions will retain suitable antimicrobial activity.

The film-forming emulsions of the present invention are used to promote asepsis on mammalian skin by (a) applying to said skin the emulsion as herein described, (b) allowing the emulsion to dry to form a film, and (c) allowing the film to remain on the skin to promote asepsis.

The film-forming emulsions may be applied to skin with a sponge or gauze, as a spray or by any other suitable means. Preferably, the film-forming emulsion is applied to skin in a thickness which provides a film which, when dry is about 0.0025 mm to 0.025 mm in thickness.

Films formed from a film-forming emulsion of this invention may be removed conveniently using a remover solution such as isopropanol. Alternatively, the film may be removed by covering with a surgical drape which includes a pressure-sensitive adhesive layer. When the surgical drape is removed, the film that is contacted by the adhesive layer of the surgical drape is also removed.

In some instances, such as in the case of burn wounds or in use on sensitive tissue, it may be desirable to simply allow the film to wear off with time as opposed to removing it.

The invention will be further clarified by a consideration of the following non-limiting examples, which are intended to be purely exemplary of the invention.

PREPARATION OF FILM-FORMING EMULSIONS

Example 1

A film-forming copolymer emulsion containing iso-octyl acrylate, methyl methacrylate and N-vinylpyrrolidone in relative amounts of 50%, 40%, and 10% by weight, respectively, was prepared by semi-continuous polymerization as follows:

To a 2-liter split resin flask fitted with a condenser, stirrer, temperature control, addition funnel and nitrogen purge was added 770 g. of deionized water, 27.6 g. of sodium lauryl sulfate solution (29.6% active, commercially available as Sipex SB TM from Alcolac, Inc., Baltimore, Md.), 8.0 g. of polyoxyethylene (20) sorbitan monostearate (commercially available as Tween 60 from ICI Americas, Inc., Wilmington Del.), 30 g. of iso-octyl acrylate, 24 g. of methyl methacrylate, 6 g. of N-vinylpyrrolidone and 0.8 g. of potassium persulfate. The flask was then heated to 70° C. accompanied by nitrogen purge and agitation at about 200 rpm. A mixture of 270 g. iso-octyl acrylate, 216 g. of methyl methacrylate, and 54 g. of N-vinylpyrrolidone was added from the addition funnel into the flask continuously over a 4 hour period while the flask temperature was maintained at 70° C. One hour after the monomer addition, the flask was cooled to 60° C., 6 g of vinyl acetate and 10 g of aqueous solution containing 0.1 g of potassium persulfate were added to the flask. Two hours later, 3.0 g of vinyl acetate was added and reaction was carried out at 60° C. for two more hours. The flask temperature was then raised to 70° C. and a vacuum of 15 mmHg was applied for 3 hours. The emulsion was then cooled to room temperature and filtered through a piece of cheese cloth. The resulting emulsion contained 46.5% solids, and had a Brookfield viscosity of 6200 cps.

Example 2

A film-forming copolymer emulsion containing iso-octyl acrylate, methyl methacrylate and N-vinylpyrrolidone in relative amounts of 50%, 40% and 10% by weight, respectively, was prepared by semi-continuous polymerization as follows:

To a 2-liter split resin flask fitted with a condenser, stirrer, temperature control, addition funnel and nitrogen purge was added 770 g. of deionized water, 8.0 g. of sodium lauryl sulfate (90% active, commercially available as Texapon K-12 TM, Henkel Co., LaGrange, IL), 8.0 g. of Tween 60 (ICI Americas, Inc.), 30 g. of distilled iso-octyl acrylate, 24 g. of methyl methacrylate, 6 g. of N-vinylpyrrolidone, 0.8 g. of potassium persulfate, and 0.8 g. of sodium bicarbonate. The flask was heated to 70° C. accompanied by nitrogen purge and agitation at about 200 rpm. A mixture of 270 g. distilled iso-octyl acrylate, 216 g. methyl methacrylate and 54 g. N-vinylpyrrolidone was added from the addition funnel into the flask continuously over a 6 hour period while the flask temperature was maintained at 70° C. After the monomer addition, the flask was kept at 70° C. for 17 hours. The emulsion was then cooled to room temperature and filtered through a piece of cheese cloth. The resulting emulsion contained 46.0% solids, and had a Brookfield viscosity of 1800 cps.

Example 3

A film-forming copolymer emulsion containing iso-octyl acrylate, methyl methacrylate and N-vinylpyrrolidone in relative amounts of 50%, 40% and 10% by weight, respectively, was prepared by semi-continuous polymerization as follows:

To a 2-liter split resin flask fitted with a condenser, stirrer, temperature control, addition funnel and nitrogen purge was added 745 g. of deionized water, 55.2 g. of sodium lauryl sulfate solution (29.6% active, commercially available as Sipex SB TM from Alcolac, Inc.), 40 g. of iso-octyl acrylate, 32 g. of methyl methacrylate, 8 g. of N-vinylpyrrolidone, and 0.80 g. of potassium persulfate. The flask was then heated to 70° C. accompanied by nitrogen purge and agitation at about 300 rpm. A mixture of 237.5 g. iso-octyl acrylate, 190 g. methyl methacrylate, and 47.5 g. N-vinylpyrrolidone was added from the addition funnel into the flask continuously over a 3 hour period while the flask temperature was maintained at 70° C. After the monomer addition, the flask was kept at 70° C. for 3.5 hours. The latex was then cooled to room temperature and filtered through a piece of cheese cloth. The resulting latex contained 41.4% solids and had a Brookfield viscosity of 4000 cps.

Example 4

A film-forming copolymer emulsion containing iso-octyl acrylate, methyl methacrylate and N-vinylpyrrolidone in relative amounts of 60%, 35% and 5% by weight, respectively, was prepared by semi-continuous polymerization as follows:

To a 2-liter split resin flask fitted with a condenser, stirrer, temperature control, addition funnel and nitrogen purge was added 821 g. of deionized water, 18.6 g. of sodium lauryl sarcosinate (30% active, commercially available as Maprosyl 30 from Onyx Chemical Co., Jersey City, N.J.), 33.6 g. of iso-octyl acrylate, 19.6 g. of methyl methacrylate, 2.8 g. of N-vinylpyrrolidone and 0.84 g. of potassium persulfate. The flask was then heated to 70° C. accompanied by nitrogen purge and agitation at about 200 rpm. A mixture of 302.4 g. iso-octyl acrylate, 176.4 g. methyl methacrylate and 25.2 g. N-vinylpyrrolidone was added from the addition funnel into the flask continuously over a 5 hour period while the flask temperature was maintained at 70° C. After the monomer addition, the flask temperature was maintained at 70° C. for 10 hours. The emulsion was then cooled to room temperature and filtered through a piece of cheese cloth The resulting emulsion contained 40.1% solids, and had a Brookfield viscosity of 53 cps.

Example 5

An emulsion is prepared in a manner similar to the above example (Example 4) except the monomers were added in the following weight ratio: 55% iso-octyl acrylate, 40% methyl methacrylate and 5% N-vinylpyrrolidone. The resulting emulsion contained 40.3% solids and had a Brookfield viscosity of 55 cps. This emulsion has a pH of 5.9 due to choice of surfactant.

Example 6

A film-forming copolymer emulsion containing iso-octyl acrylate, methyl methacrylate and N-vinylpyrrolidone in relative amounts of 50%, 40% and 10% by weight, respectively, was prepared by batch polymerization as follows:

To a quart brown glass bottle having a narrow neck was added 60 g. iso-octyl acrylate, 48 g. methyl methacrylate, 12 g. N-vinylpyrrolidone, 1.2 g. sodium lauryl sulfate (90% active, commercially available as Texapon K-12 TM from Henkel Co.), 1.2 g. of polyoxyethylene (20) sorbitan monostearate (commercially available as Tween 60 from ICI Americas, Inc., Wilmington, Del.), 0.28 g. of potassium persulfate and 280 g. of deionized water. The bottle was purged with nitrogen and then sealed and tumbled for 24 hours in a water bath maintained at 70° C. The resulting emulsion was then filtered through a piece of cheese cloth. The resulting emulsion contained 25.7% solids and had a Brookfield viscosity of 5 cps.

The following emulsions were prepared as in Example 6:

Example 7

6 g. iso-octyl acrylate, 48 g. methyl methacrylate, 6 g. N-vinylpyrrolidone.

Example 8

72 g. iso-octyl acrylate, 42 g. methyl methacrylate, 6 g. N-vinylpyrrolidone.

Example 9

72 g. iso-octyl acrylate, 36 g. methyl methacrylate, 12 g. N-vinylpyrrolidone.

Example 10

60 g. iso-octyl acrylate, 12 g. N-vinylpyrrolidone, 48 g. ethyl methacrylate.

Example 11

48 g. iso-octyl acrylate, 12 g. N-vinylpyrrolidone, 60 g. ethyl methacrylate.

Example 12

42 g. iso-octyl acrylate, 6 g. N-vinylpyrrolidone, 72 g. ethyl methacrylate.

Example 13

60 g. iso-octyl acrylate, 12 g. N-vinyl pyrrolidone, 48 g. iso-butyl methacrylate.

Example 14

60 g. iso-octyl acrylate, 12 g. N-vinylpyrrolidone, 48 g. styrene.

INCORPORATION OF ANTIMICROBIAL AGENTS

Example 15

To 80.0 g. of the emulsion of Example 3, which was gently stirred by a magnetic stir bar, was added dropwise a previously prepared solution of 0.48 g. of sodium iodide dissolved in 4 mLs of distilled water. To the resulting stirring mixture, 0.40 g. of solid iodine was added. The solid iodine did not dissolve immediately and the mixture was allowed to stir overnight after which a homogeneous mixture resulted.

Example 16

To 51.61 g. of the emulsion of Example 1, which was gently stirred by a magnetic stir bar, was added 28.39 g. of distilled water. To the resulting stirring mixture was added dropwise a previously prepared solution of 0.48 g. of sodium iodide dissolved in 10 mLs of distilled water. After the resulting mixture was allowed to stir for one hour, 0.80 g. of iodine crystals were added at the rate of 0.10 g. per 30 minutes. The resulting mixture was stirred for 24 hours at medium stirring to insure dissolution of the iodine. The stirring was then ended and the mixture was then filtered through two layers of gauze.

The above procedure was repeated changing only the amounts of the components to give the following mixtures: (All samples utilized the emulsion of Example 1).

| Example No. | Emulsion grams | Water grams | NaI/water grams/grams | Iodine grams |
| --- | --- | --- | --- | --- |
| 17 | 80.0 | 0 | 0.48/10 | 0.80 |
| 18 | 34.4 | 45.6 | 0.48/10 | 0.80 |
| 19 | 34.4 | 45.6 | 0/0 | 1.60 |
| 20 | 34.4 | 45.6 | 0.96/10 | 1.60 |
| 21 | 12.9 | 22.1 | 0.24/5 | 0.40 |
| 22 | 8.6 | 26.4 | 0.24/5 | 0.40 |
| 23 | 17.2 | 22.8 | 0/0 | 0.00 |
| 24 | 17.2 | 17.8 | 0.40/5 | 0.40 |
| 25 | 34.4 | 34.0 | 0.80/10 | 0.80 |
| 26 | 34.4 | 33.2 | 0.80/10 | 1.60 |

Example 27

To 17.39 g. of the emulsion of Example 2 was added 13.57 g. of distilled water. The mixture was brought to a medium stir with a magnetic stir bar and 0.40 g. of a buffer solution was added that was previously prepared by mixing 29.25 mLs of a 0.10 M citric acid monohydrate solution and 70.75 mLs of a 0.20 M disodium phosphate solution. A solution of 0.40 g. potassium iodate in 3.00 g. of distilled water was then added at the rate of 1 mL every 30 minutes. A solution of 0.20 g. of potassium iodide in 5.00 g. of distilled water was added at the rate of 1 mL every 30 minutes. The mixture was allowed to stir for one hour after which 0.40 g. of solid iodine crystals were added at the rate of 0.1 g. every 30 minutes. The composition was stirred for 24 hours to insure dissolution of the iodine species, after which the stirring was ended and the sample allowed to settle. The mixture was then filtered through two layers of Grade 80 bleached cotton cheesecloth (commercially available from Twin Cities Janitor Supply Co., St. Paul, Minn.).

The following samples were prepared as in Example 27 using the same buffer solution.

| Example No. | Emulsion No. | Emulsion g | Water g | KIO3/water g/g | KI/water g/g | Iodine g | Buffer Soln g |
| --- | --- | --- | --- | --- | --- | --- | --- |
| 28 | 6 | 31.1 | 0 | 0.04/1.0 | 0.20/3.6 | 0.40 | 3.60 |
| 29 | 7 | 30.5 | 0 | 0.04/1.0 | 0.20/2.0 | 0.40 | 0.60 |
| 30 | 12 | 33.5 | 0 | 0.04/2.3 | 0.20/2.3 | 0.40 | 0.60 |
| 31 | 10 | 35.1 | 0 | 0.04/1.0 | 0.20/2.0 | 0.40 | 0.60 |
| 32 | 14 | 27.6 | 0 | 0.02/.50 | 0.10/1.0 | 0.40 | 0.30 |
| 33 | 13 | 20.6 | 0 | 0.02/.60 | 0.10/1.0 | 0.20 | 0.30 |
| 34 | 2 | 17.4 | 13.4 | 0.04/3.0 | 0.20/5.0 | 0.40 | 0.60 |
| 35 | 2 | 26.1 | 4.7 | 0.04/3.0 | 0.20/5.0 | 0.40 | 0.60 |
| 36 | 2 | 34.8 | 0 | 0.04/1.0 | 0.20/3.0 | 0.40 | 0.60 |
| 37 | 2 | 17.4 | 12.7 | 0.08/3.0 | 0.40/5.0 | 0.80 | 0.60 |
| 38 | 2 | 17.4 | 13.4 | 0.02/3.0 | 0.20/5.0 | 0.40 | 0.60 |
| 39 | 2 | 17.4 | 13.3 | 0.08/3.0 | 0.20/5.0 | 0.40 | 0.60 |
| 40 | 2 | 17.4 | 21.0 | 0.04/3.0 | 0 | 0.40 | 0.20 |
| 41 | 2 | 17.4 | 13.5 | 0.04/3.0 | 0.04/5.0 | 0.40 | 0.60 |
| 42 | 2 | 17.4 | 13.3 | 0.04/3.0 | 0.30/5.0 | 0.40 | 0.60 |
| 43 | 2 | 17.4 | 13.5 | 0.04/3.0 | 0.10/5.0 | 0.40 | 0.60 |
| 44 | 2 | 17.4 | 13.4 | 0.04/1.0 | 0.20/4.0 | 0.40 | 3.60 |

Similarly, the following samples were prepared as in Example 27, except that sodium iodide was used as the iodide source instead of potassium iodide. (Each of the following contained 17.4 g. of the emulsion of Example 2.)

| Example No. | Water g. | KIO3/water g/g | NaI/water g/g | Iodine g. | Buffer Soln g. |
| --- | --- | --- | --- | --- | --- |
| 45 | 11.8 | 0 | 0.40/5.0 | 0.40 | 5.0 |
| 46 | 18.0 | 0.04/1.0 | 0.20/3.0 | 0.40 | 0 |
| 47 | 13.0 | 0.04/1.0 | 0.20/3.0 | 0.40 | 5.0 |
| 48 | 12.6 | 0.04/1.0 | 0.20/3.0 | 0.80 | 5.0 |

Example 49

To the formulation prepared in example 48, 0.8 g. of isopropyl alcohol was added dropwise with stirring.

Example 50

To 27.6 g. of the emulsion prepared in Example 8 was added 3.2 g. of distilled water. The mixture was brought to a medium stir with a magnetic stir bar. A solution of 0.0328 g. of sodium bicarbonate in 1.02 g. of distilled water was then added in two parts over 30 minutes. The resulting mixture was allowed to stir for 30 minutes and 0.6 g. of the buffer described in Example 27 above was added. A solution of 0.0413 g. of potassium iodate in 2.98 g. of water was then added at the rate of 1 mL every 30 minutes. Then 0.40 g. of solid iodine crystals were added at the rate of 0.1 g. every 30 minutes. The composition was stirred for 24 hours to insure complete dissolution of the iodine species. After the stirring was ended and the sample allowed to settle, it was filtered through two layers of Grade 80 bleached cotton cheesecloth.

Example 51

This sample was made as in Example 50, except that 31.62 g. of the emulsion of Example 4 were used, and no water was immediately added.

Example 52

This sample was made as in Example 50, except that 33.47 g. of the emulsion of Example 11 were used and no water was immediately added.

Example 53

To 19 95 of the emulsion of Example 4 was added 11.01 g. of distilled water. The mixture was brought to a medium stir with a magnetic stir bar and 0.40 g. of a previously prepared buffer solution (91.9 mL of 0.1 M sodium dihydrogen phosphate and 8.1 mLs of 0.1 M sodium monohydrogen phosphate) was added. A solution of 0.0410 g. of potassium iodate in 3.01 g. of distilled water was added at the rate of 1 mL every 30 minutes. A solution of 0.20 g. of potassium iodide in 5.01 g. distilled water was then added at the rate of 1 mL every 30 minutes. The mixture was allowed to stir for one hour. Then 0.40 g. of iodine crystals were added at the rate of 0.10 g. every 30 minutes. The mixture was stirred for 24 hours to insure dissolution of the iodine. After the stirring was ended and the sample allowed to settle, it was then filtered through two layers of Grade 80 bleached cotton cheesecloth.

Similarly the following samples were prepared. (Each of the following contained 19.95 g. of the emulsion of Example 4.)

| Example No. | Water g. | KIO₃/water g/g | KI/water g/g | Iodine g. | Buffer soln g. |
|---|---|---|---|---|---|
| 54 | 11.33 | 0.02/3 | 0.1/5 | 0.2 | 0.4 |
| 55 | 11.59 | 0.0043/3 | 0.0195/5 | 0.0418 | 0.4 |
| 56 | 10.69 | 0.16/3 | 0.4/5 | 0.8 | 0 |
| 57 | 9.25 | 0.64/3 | 0.96/5 | 0.8 | 0.4 |

Example 58

This sample was prepared as in Example 53 with 19.85 g of the emulsion of Example 5, 11.51 g of distilled water, 0.04 g of potassium iodate dissolved in 3 g of distilled water, 0.2 g of potassium iodide dissolved in 5 g of distilled water, and 0.4 g of iodine. No buffer was added. This sample was sterilized by gamma radiation as described below.

Example 59

A solution of 0.65 g of sodium iodide and 0.26 g of potassium iodate dissolved in 128 g of distilled water was added dropwise over 1 hour to 130 g of the latex of Example 5 with stirring by a magnetic stir bar. The resulting mixture was stirred for 0.5 hours after the addition was complete after which 3 g of iodine was added. The resulting mixture was stirred overnight by magnetic stir bar. The resulting dark brown homogeneous mixture was filtered through cheese cloth into a plastic bottle.

TESTING OF FILM-FORMING COMPOSITIONS

Moisture Vapor Transmission Rate

The film-forming composition of example 15 was coated on glass and allowed to dry completely. The resulting 0.025 mm thick film was removed and the moisture vapor transmission rate was measured through a circular sample of area 0.00050671 m² using the water method of ASTM Method E 96-80, to be approximately 700 g/m²·24 h at 40° C. with a 90% relative humidity differential across the film.

Preferably, a film that is about 0.025 mm thick will have a moisture vapor transmission rate of at least 600 g/m²·24h at 40° C. with a 90% relative humidity differential across the film.

Dry Time

Film-forming compositions were soaked into cotton gauze (commercially available as Curity ™ cheesecloth from The Kendall Company, Hospital Products, Boston, Mass.) and lightly coated on the shaved or clipped backs of live pigs. Cotton gauze was pressed with light finger pressure on the coated area and the time recorded when such pressing did not result in any transfer to the gauze.

| Dry Time on Live Pigs | | |
|---|---|---|
| Example | % Solids | Dry Time (min:sec) |
| 17 | 41 | 1:50–2:20 |
| 16 | 26 | 1:50–2:00 |
| 18 | 18 | 2:10 |
| 21 | 15 | 2:40–2:50 |
| 22 | 10 | 3:00–3:15 |

It was not anticipated that such short dry times would be obtained with a water based system. It is particularly surprising that dry times did not begin to rise significantly until % solids dropped to below 15% and that even with 90% water content, Example 22 dried in significantly less than 5 minutes.

Film-forming compositions were soaked into cotton gauze (commercially available as Curity ™ cheesecloth from The Kendall Company, Hospital Products, Boston, Mass.) and lightly coated on the backs of human volunteers. Cotton gauze was pressed with light finger pressure on the coated area and the time recorded when such pressing did not result in any transfer to the gauze.

| Dry Time on People | | | |
|---|---|---|---|
| Example | % Solids | % Iodine | Dry Time (min:sec) |
| 23 | 20 | 0 | 3:00–3:30 |
| 24 | 20 | 1 | 1:30–2:15 |

The composition which contained iodine dried significantly quicker than the composition without iodine species. It was not anticipated that iodine would have such a beneficial effect on the drying rate.

Film-forming compositions were soaked into cotton gauze (commercially available as Curity ™ cheesecloth from The Kendall Company, Hospital Products, Boston, Mass.) and lightly coated on the forearms of human volunteers. Cotton gauze was pressed with light finger pressure on the coated area and the time recorded when such pressing did not result in any transfer to the gauze.

| Dry Time on People | | | |
|---|---|---|---|
| Example | % Solids | % Iodine | Dry Time (min:sec) |
| 5 | 40 | 0 | 2:00–2:15 |
| 37 | 20 | 2 | 0:50 |
| 41 | 20 | 1 | 0:45–0:50 |
| 43 | 20 | 1 | 0:50 |
| 58 | 20 | 1 | 1:00 |
| Betadine ™ [1] solution | 10 | 1 | 3:00–4:00 |
| DuraPrep ™ [2] surgical solution | 8.1 | 0.5 | 0:45–0:50 |

[1] commercially available from Purdue Frederic Co., Norwalk, CT 06856.
[2] commercially available from 3M Company, St. Paul, MN The above compositions of the present invention all exhibited surprisingly short dry times for emulsion-based compositions. Dry time of less than 2.5 minutes, and preferably less than 2 minutes are observed in film-forming emulsions of the present invention. Dura-Prep TM surgical solution, which is the analogous iso-propanol based film-forming composition having a monomer ratio of 50% iso-octyl acrylate, 40% methyl methacrylate, 10% N-vinylpyrrolidone (examples 37, 41 and 43 have the same monomer ratio), exhibited a dry time that was about the same as the emulsion based solution. As a comparison, the dry time for Betadine TM solution, which is a water-soluble complex of N-vinylpyrrolidone/iodine, is unacceptably long. Additionally, Betadine TM solution does not exhibit the desired water-insoluble properties.

Elasticity, Tack and Scrub Resistance

Film-forming compositions were coated onto glass and allowed to dry, forming films approximately 0.025 mm thick. The dry films were removed with a razor blade and slowly stretched by hand for a qualitative determination of elasticity. Films which broke before any noticeable elongation were identified as very brittle, films which broke after about 5% elongation or less were identified as brittle, films which broke after about 5% to 25% elongation were identified as moderately elastic, films which broke after about 25% to 100% elongation were identified as elastic, and films which broke after 100% elongation were identified as very elastic.

As another indication of flexibility and elasticity of the film, compositions may be coated on the human elbow joint and allowed to dry to form a film. The elbow joint is flexed, and the film is inspected to determine whether cracking has occurred. Films of the present invention will survive this elbow flexion test without observable cracking.

Compositions were coated as above on human volunteers and allowed to dry. A cotton ball (long fiber virgin purified cotton USP) is then pressed against the coating with medium finger pressure. The degree of tack was determined by the amount of fibers which are transferred to the film. When no fibers were transferred the film was identified as non-tacky. Even films which were slightly tacky when pressed with a cotton ball, did not feel tacky when pressed with a surgical glove or bare finger.

The test area above was then scrubbed using light finger pressure with a saline soaked gauze for at least 40 scrubs and observed for removal of film and loss of iodine color. Samples described as excellent experienced no visible changes.

| Example | Elasticity | Tack | Scrub resistance |
|---|---|---|---|
| 28 | moderate | non-tacky | good |
| 29 | elastic | very slightly | very good |
| 50 | very elastic | slightly | excellent |
| 51 | very elastic | tacky | very good |
| 27 | moderate | non-tacky | good |
| 53 | moderate | slightly | excellent |
| 30 | moderate | non-tacky | good |
| 31 | very elastic | very tacky | good |
| 52 | very elastic | slightly | excellent |
| 32 | very elastic | very tacky | poor |
| 33 | very elastic | very tacky | poor |

It is desirable that compositions provide films with good to excellent scrub resistance and which are slightly tacky or non-tacky by the above cotton ball test. The above cotton ball tack test is particularly sensitive and the above films will all exhibit less tack to gloved or ungloved hands than they did to cotton balls. After testing a composition, adjustments in the film properties can be accomplished by changes in the monomer content, particularly by adjusting the relative amounts of the high $T_g$ and low $T_g$ contributing monomers. Sample 28 was very brittle and showed poor scrub resistance. A reduction in the relative amount of methyl methacrylate and an increase in the relative amount of iso-octyl acrylate and/or N-vinylpyrrolidone increased the elasticity of the resulting films. The film of Example 51 is tacky. An increase in the relative amount of methyl methacrylate and a decrease in the relative amount of iso-octyl acrylate and/or N-vinylpyrrolidone decreased the tack of the resulting films. By appropriately adjusting the hard and soft content of the polymer a good balance of properties was achieved in Examples 28, 29, 50, 27 and 53, each of which contained a copolymer of iso-octyl acrylate, methyl methacrylate and N-vinylpyrrolidone. A similar balance of properties may be achieved with other monomers as well. Sample 31 had good scrub resistance, but was very tacky. This was corrected by increasing the relative amount of ethyl methacrylate and decreasing the amount of iso-octyl acrylate as seen in Examples 52 and 30 (Example 30 also has a lower relative amount of N-vinylpyrrolidone), each of which exhibited a good balance of properties. Samples 32 and 33 are too tacky and need to be reformulated with lower relative amounts of iso-octyl acrylate and/or N-vinylpyrrolidone and a higher relative amount of styrene or isobutyl methacrylate.

Stability of Emulsion

Samples (5 ml sample in a 25 ml test tube, two replicates each) were placed in 49° C. oven as an accelerated test for physical stability. Samples were removed and the test ended when any major physical change was observed such as phase separation, gelation or solidification. Tests were also ended when a greater then 1 mm layer of precipitate was observed in the bottom of the test tube.

The table below lists the days at 49° C. before failure was observed.

| Example | Iodine | Iodide | Iodate | Solids | Days |
|---|---|---|---|---|---|
| 27 | 1% | 0.5% | 0.1% | 20% | >150 |
| 34 | 1% | 0.5% | 0.1% | 20% | >150 |
| 35 | 1% | 0.5% | 0.1% | 30% | >150 |
| 36 | 1% | 0.5% | 0.1% | 40% | >150 |
| 37 | 2% | 1% | 0.2% | 20% | >150 |
| 38 | 1% | 0.5% | 0.05% | 20% | >150 |
| 39 | 1% | 0.5% | 0.20% | 20% | >150 |
| 40 | 1% | 0 | 0.1% | 20% | >150 |
| 41 | 1% | 0.1% | 0.1% | 20% | >150 |
| 42 | 1% | 0.75% | 0.1% | 20% | >150 |
| 43 | 1% | 0.25% 0.1% | 20% | >150 | |
| 44 | 1% | 0.5% | 0.1% | 20% | >150 |
| 28 | 1% | 0.5% | 0.1% | 20% | 60 |
| 18 | 1% | 0.6% | 0 | 20% | 35 |
| 19 | 2% | 0 | 0 | 20% | 12 |
| 20 | 2% | 1.2% | 0 | 20% | 7 |
| 1 | 0 | 0 | 0 | 46% | 78 |

It is desirable to prepare film-forming emulsions that will be shipped to various destinations where they may not be used for several years. Long term aging is therefore an important factor in the selection of useful formulations of this invention. Since these samples are polymer-in-water emulsion systems, the primary concern is one of phase destabilization which is seen as precipitation, increases in viscosity, gelation, coagulation or other readily observable changes in physical make up. A goal of greater then 90 days stability at elevated temperature was set for those samples that would need long term room temperature shelf life. The above tests indicated that sample 28, which utilized emulsions prepared by batch polymerization, was less stable then analogous samples which utilized emulsions prepared by semi-continuous polymerization. The effect of added iodate anions is particularly surprising and interesting. The emulsions of Examples 18, 19 and 20, which were prepared without added iodate, are significantly less stable then analogous samples with iodate anions.

Antimicrobial Activity

Several samples were evaluated for in-vivo antimicrobial activity. Each sample was thinly coated with sample soaked cotton gauze onto the backs of subjects whose backs were seeded with Staphylococcus aureus. Different areas of the back were tested for baseline bacterial ($10^{6.3}$ to $10^{6.5}$) counts and for log reductions in bacteria after application of samples. The test method used was the Williamson and Klugman scrub cup technique (J. Invest. Dermatol. 72, 165–170). Samples were evaluated after 2 minutes, 5 minutes, and 3 hours. After allowing the sample to remain on the skin for the specified time the formulations were removed, residual antimicrobial agent neutralized, and the viable bacteria were removed and counted by the Williamson and Klugman scrub cup technique. The results are presented as an average of 6 replicates.

| Example | Log Reduction | | |
|---|---|---|---|
| | 2 min. | 5 min. | 3 hr. |
| 25 | 4.7 | 5.3 | 4.7 |
| 45 | 5.4 | 5.1 | 4.9 |
| 46 | 5.4 | 5.2 | 5.1 |
| 47 | 5.3 | 5.0 | 5.2 |
| 26 | 5.2 | 5.2 | 5.1 |
| 48 | 5.2 | 5.0 | 5.3 |
| 49 | 5.2 | 5.2 | 5.2 |

All evaluated samples provided excellent reduction in bacteria at both short and long times.

Irradiation

Several samples (Examples 16, 17, 18, 20, 21, 22, 24, 56 and 58) were irradiated at 2.5 to 3.5 MRad of cobalt gamma radiation. In all cases there were no significant changes in color, physical appearance or dry time.

pH

Of the 5 emulsions (Examples 1, 2, 3, 4, and 5) prepared by the semi-continuous method, 2 emulsions (Examples 1, 3) were acidic (pH about 3) and 3 emulsions (Examples 2, 4, 5) had more neutral pH (pH of 5 to 8). The lower pH emulsions may lead to less stable final formulations unless the pH is altered. The more neutral emulsions possibly may be used without adjusting the pH or adding buffer.

It is intended that the specification and examples be considered as exemplary only, with the true scope and spirit of the invention being indicated by the following claims.

We claim:

1. A film-forming emulsion, comprising:
(a) a substantially water resistant film-forming copolymer phase comprising A, B and C monomers wherein
   A is a monomer wherein the corresponding homopolymer has a glass transition temperature less than about $-15°$ C., and is present as about 15 to 80% of the total weight of all monomers in the copolymer,
   B is a monomer wherein the corresponding homopolymer has a glass transition temperature of more than about $-5°$ C., and is present as about 20 to 70% of the total weight of all monomers in the copolymer, and
   C is a monomer capable of complexing iodine and delivering it to the skin and is present as about 1 to 15% of the total weight of all monomers in the copolymer;
(b) about 0.05 to 15% of iodine based on total emulsion weight;
(c) an effective amount of an emulsifying agent; and
(d) about 30 to 95% by weight of water; said monomers in the copolymer phase selected such that said emulsion, when applied to human skin in an amount sufficient to form a film having a thickness of about 0.01 mm., dries in less than five minutes to form a film having the properties of
   (i) being hydrophobic, as determined by scrubbing the film using light finger pressure with a saline-soaked gauze for at least 40 scrubs with no observable removal of film or loss of iodine color, and
   (ii) being capable of elongating at least about 5% before breaking.

2. A film-forming emulsion according to claim 1, wherein the A monomer is selected from the group consisting of a monomeric acrylic or methacrylic acid ester of an alkyl alcohol containing a single hydroxyl, the alcohol having from 2 to about 14 carbon atoms when the A monomer is an acrylic acid ester, and about 7 to 18 carbon atoms when the A monomer is a methacrylic acid ester; butadiene; isoprene; N-octylacrylamide; butoxyethylene; propoxyethylene; octyloxyethylene; 1,1-dichloroethylene; vinyl versatate; vinyl caprate; and vinyl laurate;
   the B monomer is selected from the group consisting of a monomeric methacrylic acid ester of an alkyl alcohol containing a single hydroxyl, the alcohol being further described as having from 1 to about 6 carbon atoms; benzyl methacrylate, cyclohexyl methacrylate; isobornyl methacrylate; N-t-butylmethacrylamide; isobornyl acrylate; N-butylacrylamide; N-t-butylacrylamide; diethyl itaconate; diethyl fumarate; acrylonitrile; methacrylonitrile; vinyl acetate; vinyl propionate; styrene; α-methyl styrene; and vinyl toluene; and
   the C monomer is selected from the group consisting of an N-vinyl lactam and a monomer containing a polyether functionality.

3. A film-forming emulsion according to claim 1, further comprising an inorganic iodide being added as sodium or potassium iodide in an amount by weight of about 5% to 300% of the weight of said iodine.

4. A film-forming emulsion according to claim 1, further comprising inorganic iodate being added as sodium or potassium iodate in an amount by weight of about 1 to 30% of the weight of said iodine.

5. A film-forming emulsion according to claim 1, wherein the emulsion is stable at 49° C. for at least 90 days.

6. A film-forming emulsion according to claim 1, wherein the emulsion, when applied to human skin in an amount sufficient to form a film having a thickness of about 0.01 mm., has a dry time of less than 2.5 minutes.

7. A film-forming emulsion according to claim 1, further comprising about 5 to 300% inorganic iodide and about 0.1 to 100% inorganic iodate, both based on added iodine.

8. A film-forming emulsion comprising
 (a) a substantially water resistant film-forming copolymer phase comprising A, B and C monomers wherein
  the A monomer is a monomeric acrylic or methacrylic acid ester of an alkyl alcohol containing a single hydroxyl, the alcohol having from 2 to about 14 carbon atoms when the A monomer is an acrylic acid ester, and about 7 to 18 carbon atoms when the A monomer is a methacrylic acid ester, the corresponding homopolymer of said A monomer having a glass transition temperature of less than about $-15°$ C. and said A monomer being present as about 15 to 80% of the total weight of all monomers in the copolymer;
  the B monomer is a monomeric methacrylic acid ester of an alkyl alcohol containing a single hydroxyl, the alcohol being further described as having from 1 to about 6 carbon atoms, the corresponding homopolymer said B monomer having a glass transition temperature of more than about $-5°$ C. and said B monomer being present as about 20 to 70% of the total weight of all monomers in the copolymer; and
  the C monomer is an N-vinyl lactam and is present as about 1 to 15% of the total weight of all monomers in the copolymer,
 (b) about 0.05 to 15% of iodine based on total emulsion weight;
 (c) an effective amount of an emulsifying agent; and
 (d) about 30 to 95% by weight of water based on total emulsion weight.

9. A film-forming emulsion according to claim 8, wherein said iodine is present in an amount by weight of about 0.10 to 5% of the total weight of said film-forming emulsion 10. A film-forming emulsion according to claim 9, wherein said iodine is present in an amount by weight of about 0.25 to 2% of the total weight of said film-forming emulsion 11. A film-forming emulsion according to claim 8 for use on sensitive areas, wherein said iodine is present in an amount by weight of about 0.05 to 0.25% of the total weight of said film-forming emulsion.

12. A film-forming emulsion according to claim 8, further comprising about 5 to 300% an inorganic iodide based on added iodine.

13. A film-forming emulsion according to claim 12, said inorganic iodide being added as sodium or potassium iodide in an amount by weight of about 5 to 100% of the weight of said iodine.

14. A film-forming emulsion according to claim 8, further comprising about 0.1 to 100% inorganic iodate based on added iodine.

15. A film-forming emulsion according to claim 14, said inorganic iodate being added as sodium or potassium iodate in an amount by weight of about 1 to 30% of the weight of said iodine.

16. A film-forming emulsion according to claim 8, wherein the pH of said emulsion is between about 3 and 8.

17. A film-forming emulsion according to claim 16, wherein the pH of said emulsion is between about 5 and 7.

18. A film-forming emulsion according to claim 8, wherein the emulsion is stable at 49° C. for at least 90 days.

19. A film-forming emulsion according to claim 8, wherein the emulsion, when applied to human skin an amount sufficient to form a film having a thickness of about 0.01 mm., has a dry time of less than 2.5 minutes.

20. A film-forming emulsion according to claim 19, wherein the emulsion, when applied to human skin in an amount sufficient to form a film having a thickness of about 0.01 mm., has a dry time of less than 2 minutes.

21. A film-forming emulsion according to claim 8, further comprising about 5 to 300% inorganic iodide and about 0.1 to 100% inorganic iodate, both based on added iodine.

22. A film-forming emulsion of claim 8 comprising
 (a) a substantially water resistant film-forming copolymer phase comprising
  about 50 to 60% by weight of iso-octyl acrylate based on the total copolymer weight,
  about 35 to 45% by weight of methyl methacrylate based on the total copolymer weight,
  and about 5 to 10% by weight of N-vinylpyrrolidone based on the total copolymer weight;
 (b) about 1-2% of iodine based on total emulsion weight;
 (c) an effective amount of an emulsifying agent;
 (d) about 55 to 85% by weight of water based on total emulsion weight;
 (e) about 5 to 100% by weight of iodide based on added iodine; and
 (f) about 2.5 to 20% by weight of iodate based on added iodine.

* * * * *

UNITED STATES PATENT AND TRADEMARK OFFICE
CERTIFICATE OF CORRECTION

PATENT NO. : 4,978,527
DATED : December 18, 1990
INVENTOR(S) : Brink et al.

It is certified that error appears in the above-identified patent and that said Letters Patent is hereby corrected as shown below:

Col. 12, line 19, "6 g." should be --66 g.--.

Col. 13, bottom table, Example No. 30 under column KI/water, "0.20/2.3" should be --0.20/3.0--.

Col. 15, line 1, "19 95" should be --19.95--.

Col. 18, table, Example 43, columns should be:
1%, 0.25%, 0.1%, 20%, >150
delete next line "0.1%".

Signed and Sealed this

Thirteenth Day of July, 1993

Attest:

MICHAEL K. KIRK

Attesting Officer    Acting Commissioner of Patents and Trademarks